United States Patent [19]
Dahlgren

[11] 4,156,076
[45] May 22, 1979

[54] PROCESS FOR THE CONVERSION OF LACTOSE INTO MONOSACCHARIDES AND DERIVATIVES THEREOF

[75] Inventor: Stig Å. Dahlgren, Lidingö, Sweden

[73] Assignee: Carbos AG, Switzerland

[21] Appl. No.: 672,314

[22] Filed: Mar. 31, 1976

[51] Int. Cl.[2] ................................ C07H 3/02

[52] U.S. Cl. ................................ 536/1; 260/347.9; 424/49; 424/180; 568/863

[58] Field of Search ............... 536/1, 115; 260/635 C, 260/347.9

[56] References Cited

U.S. PATENT DOCUMENTS

| | | | |
|---|---|---|---|
| 2,292,293 | 8/1942 | Rose | 260/635 C |
| 2,518,235 | 8/1950 | Hartstra et al. | 260/635 C |
| 2,938,898 | 5/1960 | Werner et al. | 536/115 |
| 3,481,836 | 12/1969 | Nomura et al. | 260/635 C |
| 3,622,560 | 11/1971 | Hindley et al. | 536/1 |
| 3,632,802 | 1/1972 | BeMiller et al. | 536/1 |
| 3,705,039 | 12/1972 | Mitsuhashi et al. | 536/1 |
| 3,755,294 | 8/1973 | Walon | 536/1 |
| 3,864,166 | 2/1975 | Barker et al. | 536/1 |

*Primary Examiner*—Johnnie R. Brown
*Attorney, Agent, or Firm*—Gordon W. Hueschen

[57] ABSTRACT

The invention relates to a process for the conversion of lactose into useful monocarbohydrates, comprising the steps of oxidatively hydrolyzing a lactose solution to form galactose and gluconic acid, and separating these two constituents.

20 Claims, No Drawings

PROCESS FOR THE CONVERSION OF LACTOSE INTO MONOSACCHARIDES AND DERIVATIVES THEREOF

The present invention relates to a process for the conversion of the carbohydrate lactose into useful monocarbohydrates and optionally furfural.

In the dairy industry several by-products are obtained, among which may be mentioned whey obtained in cheese production. Whey is an aqueous suspension containing mainly lactose and also protein. The lactose content of whey is about 5% by weight, whereas the protein content thereof is about 1% by weight.

Whey is produced to-day in such amounts as to constitute an environmental problem and up to the present no practical utility for whey has been devised. Some part of the lactose may be used for producing lactic acid and lactates by fermenting the lactose, but the limited utility of these products is totally insufficient to solve the whey problem. The whey protein is perhaps easier to find practical uses for, in that the protein is rich in glycine and therefore valuable as a supplement to i.a. vegetabilic foodstuffs. However, due to the great amounts of lactose arising from protein separation (usually by so-called membrane technique), it has not up to now been economically feasible to separate the protein due to the fact that no practical uses have been available for the lactose thereby obtained.

As is well known lactose is a disaccharide which, upon hydrolysis, yields one molecule of glucose and one molecule of galactose. These two hexoses are, however, difficult to separate in an economical way due to their similarity. Lactose as such finds some use in dietary foods and pharmaceutical products, but the demand is far less than its abundant occurrence in whey.

The present invention has for its purpose to provide a process for the conversion of lactose into useful products.

Particularly, one major object of the invention is to provide a process for the conversion of lactose into monocarbohydrates which are useful as anti-caries sugars.

Another object of the invention is to provide a process whereby at least part of the monocarbohydrates obtained are converted into furfural.

It has been found, in accord with the invention, that a highly useful way of converting lactose into beneficial and useful intermediates and end products is to perform oxidative hydrolysis of a lactose solution to form galactose and gluconic acid, which are then separated and recovered. The separation of these two constituents can be done by recovering the galactose from the solution by crystallization, the gluconic acid being left in the solution.

Starting from the above separation of galactose and gluconic acid, it is now possible to proceed to highly useful end products. Thus, the galactose may be hydrogenated, at least part of it, to form the carbohydrate galactitol, which is a very beneficial sugar with regard to inhibiting the formation of caries in the dental plaque. On the other hand, the gluconic acid may be transformed to arabinose by oxidative decarboxylation of the gluconic acid in solution. Arabinose is a highly useful pentose, since it can be, on the one hand, for example by distillation under acid conditions, transferred to furfural, and on the other hand the arabinose may be hydrogenated to form arabinitol. This carbohydrate is also highly useful as an anti-caries sugar.

Thus, it can be seen that by oxidatively hydrolyzing lactose to form galactose and gluconic acid, which are then separated, highly useful end products may be produced in high yields.

The oxidation of the lactose in aqueous solution is suitably performed under mild oxidizing conditions and can be carried out for example with bromine, hydrogen peroxide, dilute nitric acid, peracids, or the like. The oxidation proceeds more easily at an increased temperature up to a maximum of about 75° C. The temperature must not be allowed to exceed about this limit, since excessive temperature can lead to undesired decomposition of the carbohydrate.

The hydrolysis of the lactobionic acid, which is formed as an intermediary product, is suitably performed in a weakly acid milieu. Useful acids are dilute mineral acids, such as hydrochloric acid, sulphuric acid, or weak organic acids, such as carboxylic acids, e.g. acetic acid, propionic acid, benzoic acid, phthalic acid, succinic acid, and the like.

The oxidative hydrolysis of the lactose in aqueous solution may be carried out by using di-functional reagents, like peracids and nitric acid. Among the peracids, peracetic acid is the preferred oxidizing acid, but other peracids, such as perbenzoic and monoperphthalic may also be used. It is immaterial whether the peracid is generated in situ by addition of hydrogen peroxide to the carboxylic acid, or if the peracid is preformed.

The oxidation of the gluconic acid to form arabinose is also carried out with mild oxidizing agents, preferably while using a catalyst. As catalysts may be used ferric and copper salts, chromium, molybdenum and vanadium oxides on alumina, and palladium or platinum on a carrier, such as charcoal. As an oxidizing agent may be used the agents mentioned above in connection with the oxidation of lactose, and a particularly preferred oxidizing agent is hydrogen peroxide and a source of $Fe^{3+}$ -ions, for example ferric acetate.

The hydrogenation of arabinose to arabinitol and galactose to galactitol is preferably carried out by catalytic hydrogenation with hydrogen under increased pressure. As a catalyst there may be used in a conventional manner nickel and copper salts, nickel or kieselguhr, platinum or palladium on a carrier, mixed oxides of copper and chromium and sulphides of molybdenum and tungsten. Particularly preferred are palladium or platinum on a carrier, such as charcoal.

The step of converting arabinose to furfural is conventional in the art and is suitably carried out by steam distillation under acid conditions.

It has been established that saccharose, which is the sweetener most widely used, has a desisive influence on the presence of caries. Thus, there has been reason to look for other carbohydrates and to investigate their odontological and other effects on the teeth. It has been found that i.a. the hexose galactitol and the pentose arabinitol have a marked influence with regard to inhibiting the formation of dental caries. It has been suggested that the caries-inhibiting sugars do not generate low pHs when contacted by the saliva of the mouth, whereby under favourable conditions even remineralization of the dental plaque may occur. The two carbohydrates galactitol and arabinitol as produced in accord with the instant invention have been disclosed to have these favourable characteristics.

The invention will now be further described by non-limiting examples.

EXAMPLE 1

Preparation of D-galactose

To a solution of 50 g whey lactose in 150 ml of water there is added 1 ml of concentrated hydrochloric acid and ½ g of bromine. The mixture is heated to about 35° C. on a water bath. After a reaction period of about 1 hour under stirring, the solution becomes completely clear. The D-galactose is separated by evaporation in vacuo and is precipitated in the form of white crystals.

EXAMPLE 2

Preparation of D-arabinose

The aqueous solution remaining after separating the galactose is subjected to oxidation by adding 25 ml 35 % aqueous solution of hydrogen peroxide and ferric acetate in a catalyzing amount (a few grams). The temperature is raised under stirring to about 70° C. and the reaction takes place over a period of time of 45 minutes. After cooling, the solution is filtered to remove residual iron salt. A water-clear solution results.

EXAMPLE 3

Preparation of furfural

An aliquot of the arabinose solution from Example 2 above is taken to furfural production. In a test reactor the arabinose solution is subjected to steam distillation (12 ats, 186° C.) and furfural is obtained in the overhead vapours leaving the reactor.

EXAMPLE 4

Preparation of arabinitol

Another aliquot of the arabinose solution obtained from Example 2 above is subjected to hydrogenation, in that hydrogen is passed into the solution after adding 10% palladium on charcoal thereto as a catalyst. After about 25 minutes the reaction is completed, and arabinitol is obtained by evaporation in vacuo in the form of white crystals.

EXAMPLE 5

Preparation of galactitol

The galactose obtained from Example 2 above is redissolved in water and catalytic hydrogenation and crystallization are performed as under (c) above. D-galactitol is obtained in the form of white crystals.

EXAMPLE 6

The procedure of Example 1 is repeated while using nitric acid as an oxidizing agent in an amount to make the aqueous lactose solution have a concentration of 1 N. The same useful result is obtained.

EXAMPLE 7

The procedure of Example 1 is repeated while using peracetic acid as an oxidizing agent in an amount to make the aqueous lactose solution 1 N with regard to peracetic acid. The same result is obtained.

EXAMPLE 8

The procedure of Example 2 is repeated but using for the oxidation peracetic acid in a slight excess over 1 mole acid per mole gluconic acid and 10% platinum on charcoal as a catalyst. The same useful result is obtained.

EXAMPLE 9

The procedure of Example 8 is repeated but the peracetic acid used for the oxidation is replaced by perbenzoic acid. The same result is obtained.

EXAMPLE 10

The procedure of Example 4 is repeated while using Raney nickel as a catalyst. The same result in obtained.

EXAMPLE 11

The procedure of Example 5 is repeated while using Raney nickel as a catalyst. D-galactitol is obtained in a good yield.

The instant invention is not delimited to the above specific examples and many alterations and modifications can be made with regard to the process details thereof. As a common denominator to all variants and embodiments of the invention stands the oxidative hydrolysis of the lactose to form galactose and gluconic acid which are then separated. This basic concept makes it possible to proceed with the preparation of the highly useful end products as described earlier in this specification.

It is to be understood that the invention is not to be limited to the exact details of operation or exact compounds, compositions, methods, or procedures shown and described, as many modifications and equivalents of the process illustrated in the foregoing will be apparent to one skilled in the art and may be made in the method and procedure of the present invention without departing from the spirit or scope thereof.

What is claimed is:

1. A process for the conversion of lactose into mono-carbohydrates, comprising the steps of oxidatively hydrolyzing a lactose solution to form galactose and gluconic acid, and separating these two constituents.

2. A process according to claim 1, wherein the oxidative-hydrolysis is carried out using bromine and hydrochloric acid.

3. A process according to claim 1, comprising the further step of oxidative decarboxylation of the gluconic acid to form arabinose.

4. A process according to claim 3, wherein the oxidative decarboxylation is carried out using hydrogen peroxide and a source of $Fe^{3+}$-ions.

5. A process according to claim 3, comprising the further step of converting at least part of the arabinose to furfural.

6. A process according to claim 5, wherein said conversion is performed by steam distillation under acid conditions.

7. A process according to claim 1, comprising the further step of hydrogenating at least part of the galactose to form galactitol.

8. A process according to claim 7, wherein the hydrogenation is carried out using hydrogen gas and palladium on charcoal as a catalyst.

9. A process according to claim 1, comprising the further step of hydrogenating at least part of the galactose to form galactitol, and also comprising the further step of oxidative decarboxylation of the gluconic acid to form arabinose.

10. A process according to claim 9, wherein the hydrogenation is carried out using hydrogen gas and palladium on charcoal as a catalyst.

11. A process according to claim 1, comprising the further step of hydrogenating at least part of the galactose to form galactitol, and also comprising the further step of converting at least part of the arabinose to furfural.

12. A process according to claim 11, wherein the hydrogenation is carried out using hydrogen gas and palladium on charcoal as a catalyst.

13. A process according to claim 3, comprising the further step of hydrogenating at least part of the arabinose to arabinitol.

14. A process according to claim 13, wherein the hydrogenation is carried out using hydrogen gas and palladium on charcoal as a catalyst.

15. A process according to claim 13, comprising the further step of hydrogenating at least part of the galactose to form galactitol.

16. A process according to claim 15, wherein the hydrogenation is carried out using hydrogen gas and palladium on charcoal as a catalyst.

17. A process for converting lactose into monocarbohydrates and furfural, comprising:

(a) oxidatively hydrolyzing an acid aqueous solution of lactose to form a solution of D-galactose and D-gluconic acid;

(b) recovering the D-galactose from the solution by crystallization leaving the D-gluconic acid in the solution;

(c) redissolving at least part of the D-galactose and hydrogenating the D-galactose in solution to form D-galactitol which is recovered;

(d) oxidatively decarboxylating the D-gluconic acid in solution to form a solution of D-arabinose; and (e) converting at least part of the D-arabinose to furfural by distillation under acid conditions and recovering the furfural formed.

18. A process according to claim 17, wherein the oxidative-hydrolysis is carried out using bromine and hydrochloric acid; the hydrogenation is carried out using hydrogen gas and palladium on charcoal as a catalyst; the oxidative decarboxylation is carried out using hydrogen peroxide and a source of $Fe^{3+}$-ions; and the conversion of the D-arabinose to furfural is carried out by steam distillation in the presence of sulfuric acid.

19. A process according to claim 17, comprising the further step of hydrogenating part of the D-arabinose to form D-arabinitol.

20. A process according to claim 19, wherein the hydrogenation is carried out using hydrogen gas and palladium on charcoal as a catalyst.

* * * * *

UNITED STATES PATENT AND TRADEMARK OFFICE
CERTIFICATE OF CORRECTION

PATENT NO. : 4,156,076

DATED : May 22, 1979

INVENTOR(S) : Dahlgren

It is certified that error appears in the above-identified patent and that said Letters Patent are hereby corrected as shown below:

Col. 2, line 46; "nickel or kieselguhr" should read -- nickel on kieselguhr --
Col. 2, line 55; "desisive" should read -- decisive --

Signed and Sealed this

*Sixth* Day of *November 1979*

[SEAL]

*Attest:*

RUTH C. MASON
*Attesting Officer*

LUTRELLE F. PARKER
*Acting Commissioner of Patents and Trademarks*